United States Patent
Avrutov et al.

(10) Patent No.: US 7,129,358 B2
(45) Date of Patent: Oct. 31, 2006

(54) PROCESSES FOR THE PRODUCTION OF SUBSTITUTED 2-(2-PYRIDYLMETHYL) SULFINYL-1H-BENZIMIDAZOLES

(75) Inventors: Ilya Avrutov, Bat Hefer (IL); Marioara Mendelovici, Rechovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 48 days.

(21) Appl. No.: 10/066,850

(22) Filed: Feb. 4, 2002

(65) Prior Publication Data
US 2003/0036554 A1  Feb. 20, 2003

Related U.S. Application Data

(60) Provisional application No. 60/266,162, filed on Feb. 2, 2001.

(51) Int. Cl.
*C07D 401/12* (2006.01)
(52) U.S. Cl. .................................. 546/273.7
(58) Field of Classification Search ............... 546/113, 546/273.7
See application file for complete search history.

(56) References Cited

U.S. PATENT DOCUMENTS 5,039,806 A * 8/1991 Brandstorm et al.
5,391,752 A   2/1995 Hoerrner et al. ......... 546/273.4
5,578,732 A  11/1996 Kato et al.
6,303,787 B1 10/2001 Prasad
2003/0036554 A1 2/2003 Avrutov et al.

FOREIGN PATENT DOCUMENTS

| CA | 1127158 | 7/1982 |
| CA | 1263119 | 11/1989 |
| EP | 533264 | 3/1993 |
| ES | 2 063 705 | 1/1995 |
| GB | 2069492 | 8/1981 |
| WO | WO91/18895 | 12/1991 |
| WO | WO99/25711 | 5/1999 |
| WO | 9929299 * | 7/1999 |
| WO | 9947514 * | 9/1999 |
| WO | WO 00/02876 A1 | 1/2000 |
| WO | WO 01/68594 A1 | 9/2001 |
| WO | WO 02/062786 | 8/2002 |

OTHER PUBLICATIONS

Sharpless et al., "Aldrichimica Acta," 12:63 (1979).
Choudray et al., J. Mol. Catalysts, 75:L7-12 (1992).

* cited by examiner

*Primary Examiner*—Patricia L. Morris
(74) *Attorney, Agent, or Firm*—Kenyon & Kenyon LLP

(57) ABSTRACT

Improved processes for preparing substituted 2-(2-pyridylmethyl)sulfinyl-1H-benzimidazoles are disclosed.

7 Claims, No Drawings

PROCESSES FOR THE PRODUCTION OF SUBSTITUTED 2-(2-PYRIDYLMETHYL) SULFINYL-1H-BENZIMIDAZOLES

CROSS-REFERENCE TO RELATED APPLICATION

This invention claims the benefit under 35 U.S.C. §1.119(e) of provisional application Ser. No. 60/266,162, filed Feb. 2, 2001.

FIELD OF THE INVENTION

The present invention relates to novel processes of preparing substituted 2-(2-pyridylmethyl)sulfinyl-1H-benzimidazoles.

BACKGROUND OF THE INVENTION

Several substituted 2-(2-pyridylmethyl)sulfinyl-1H-benzimidazoles are known gastric proton pump inhibitors. These include omeprazole (5-methoxy-2-[[(4-methoxy-3,5-dimethyl-2-pyridyl)methyl]sulfinyl]-1H-benzimidazole), lansoprazole (2-[[[3-methyl-4-(2,2,2-trifluoro-ethoxy)-2-pyridinyl]methyl]sulfinyl]-1H-benzimidazole), pantoprazole (5-(difluoromethoxy)-2-[[(3,4-dimethoxy-2-pyridinyl)methyl]sulfinyl]-1H-benzimidazole, and rabeprazole (2-[[[4-(3-methoxy-propoxy)-3-methyl-2-pyidinyl]methyl]sulfinyl]-1H-benzimidazole. For example, omeprazole is a proton pump inhibitor commercially available for the treatment of gastric ulcers. The compound is disclosed in European Patent No. 5318.

The reported synthesis of these substituted 2-(2-pyridylmethyl)sulfinyl-1H-benzimidazoles principally involves generally an oxidation process of a thioether moiety to form a thioester moiety of the compound of formula A:

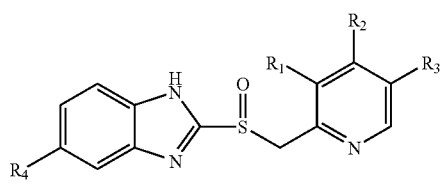

Various methods employing various different oxidants to perform this oxidation are known. For example, Canadian Patent No. 1,263,119 describes the use of hydrogen peroxide over a vanadium catalyst (such as vanadium pentoxide, sodium vanadate and vanadium acteylacetonate). Canadian Patent No. 1,127,158 similarly describes the use of peracids, peresters, ozone, etc. European Patent Application, Publication No. 533,264 describes the use of magnesium monoperoxyphthalate as the oxidizing agent. PCT Publication No. WO91/18895 describes the use of m-chloroperoxy benzoic acid as the oxidizing agent. GB Pat. No.2,069,492 generally describes this acid and other peroxy acids in the oxidation of substituted (phenylthiomethyl)pyridines.

Use of tert-butyl hydroperoxide (TBHP) as an oxidant has already been suggested for the performance of various organic oxidations. Sharpless et al., Aldrichimica Acta 12:63 (1979) review the use of THBP as an oxidant and compared with hydrogen peroxide and other peracids. Sharpless et al. describe the use of TBHP in the epoxidation of olefinic alcohols in the presence of $VO(acac)_2$ or $Mo(CO)_5$ catalysts. The oxidation of sulphides, however, is not described.

In an effort to develop a method for the selective oxidation of sulphides to sulphoxides, Choudray et al., J. Mol. Catalysts, 75:L7–L12 (1992) describe the use of TBHP in the presence of vanadium pillared clay. The results demonstrated selectivity for the oxidation to sulphoxide in preference to the sulphone far superior to that of known TBHP/vanadium catalysts. The use of $VO(acac)_2$ or $V_2O_5$ resulted in sulphones rather than sulfoxide predominating in the final product.

There has been a long felt need for efficient and safe methods for the selective oxidation of a thioether moiety of formula B to a thioester moiety of formula A. The present invention provides efficient and safe methods of preparing various substituted 2-(2-pyridylmethyl)sulfinyl-1H-benzimidazoles.

SUMMARY OF THE INVENTION

The present invention provides a process for preparing a thioester compound of formula A:

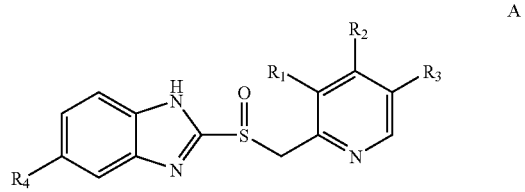

wherein $R_1$, $R_2$, and $R_4$ are each selected from the group consisting of hydrogen, substituted or unsubstituted lower alkyl and substituted or unsubstituted lower alkoxy; and $R_3$ is selected from the group consisting of hydrogen and substituted or unsubstituted lower alkyl, comprising reacting a thioether compound of formula B

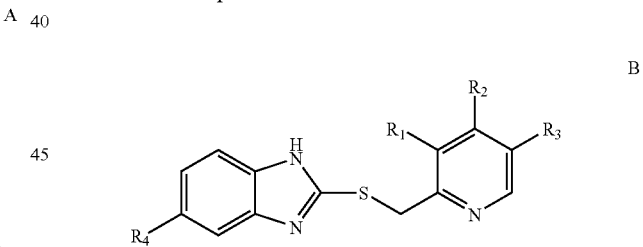

wherein $R_1$ through $R_4$ are as in formula A, with an oxidizing agent to produce selective oxidation of the thioether compound of formula B to form the thioester compound of formula A.

The present invention further provides a process for preparing a thioester compound of compound of formula A, comprising reacting a thioether compound of formula B with Oxone® (Oxone monopersulphate).

The present invention further provides a process for preparing a thioester compound of compound of formula A, comprising reacting a thioether compound of formula B with tert-butyl hydroperoxide (TBHP) in the presence of a catalyst selected from the group consisting of vanadyl (IV) acetylacetonate, sodium metavanadate and vanadium pentoxide.

The substituted 2-(2-pyridylmethyl)sulfinyl-1H-benzimidazoles prepared according to the process of the present invention yield the desired products in a relatively high yield with only small amounts of the corresponding sulphone as by-product.

An object of the present invention is to provide an improved process of selective oxidation of 5-methoxy-2-[[(4-methoxy-3,5-dimethyl-2-pyridyl)methyl]thio]-1H-benzimidazole (MPB) that utilizes a non-hazardous oxidant and results in the selective production of 5-methoxy-2-[[(4-methoxy-3,5-dimethyl-2-pyridyl)methyl]sulfinyl]-1H-benzimidazole (omeprazole), i.e., the corresponding sulphoxide, with only minor amounts of 5-methoxy-2[[(4-methoxy-3,5-dimethyl-2-pyridyl)methyl]sulphonyl]benzimidazole.

Another object of the present invention is to provide an improved process of selective oxidation of 2-[[[3-methyl-4-(2,2,2-trifluoro-ethoxy)-2-pyridinyl]methyl]thio]-1H-benzimidazole that utilizes a non-hazardous oxidant and results in the selective production of 2-[[[3-methyl-4-(2,2,2-trifluoro-ethoxy)-2-pyridinyl]methyl]sulfinyl]-1H-benzimidazole (lansoprazole), i.e., the corresponding sulphoxide, with only minor amounts of 2-[[[3-methyl-4-(2,2,2-trifluoro-ethoxy)-2-pyridinyl]methyl]sulphonyl]-1H-benzimidazole.

Another object of the present invention is to provide an improved process of selective oxidation of 5-(difluoromethoxy)-2-[[(3,4-dimethoxy-2-pyridinyl)methyl]thio]-1H-benzimidazole that utilizes a non-hazardous oxidant and results in the selective production of 5-(difluoromethoxy)-2-[[(3,4-dimethoxy-2-pyridinyl)methyl]sulfinyl]-1H-benzimidazole (pantoprazole), i.e., the corresponding sulphoxide, with only minor amounts of 5-(difluoromethoxy)-2-[[(3,4-dimethoxy-2-pyridinyl)methyl]sulphonyl]-1H-benzimidazole.

Another object of the present invention is to provide an improved process of selective oxidation of 2-[[[4-(3-methoxy-propoxy)-3-methyl-2-pyidinyl]methyl]thio]-1H-benzimidazole that utilizes a non-hazardous oxidant and results in the selective production of 5-methoxy-2-[[(4-methoxy-3,5-dimethyl-2-pyridyl)methyl]sulfinyl]-1H-benzimidazole (rabeprazole), i.e., the corresponding sulphoxide, with only minor amounts of 5-methoxy-2[[(4-methoxy-3,5-dimethyl-2-pyridyl)methyl]sulphonyl]-1H-benzimidazole.

Another object of the present invention is to provide an improved process of preparing omeprazole while the amount of 5-methoxy-2-[[(4-methoxy-3,5-dimethyl-2-pyridyl)methyl]sulphonyl]-1H-benzimidazole (SOMP) as by-product when the reaction proceeds to completion, is typically within the range of about 1 to about 4.5% by weight of the crude product mixture.

Another object of the present invention is to provide an improved process of preparing lansoprazole while the amount of 2-[[[3-methyl-4-(2,2,2-trifluoro-ethoxy)-2-pyridinyl]methyl]sulphonyl]-1H-benzimidazole as by-product when the reaction proceeds to completion, is typically within the range of about 1 to about 4.5% by weight of the crude product mixture.

Another object of the present invention is to provide an improved process of preparing pantoprazole while the amount of 5-(difluoromethoxy)-2-[[(3,4-dimethoxy-2-pyridinyl)methyl]sulphonyl]-1H-benzimidazole as by-product when the reaction proceeds to completion, is typically within the range of about 1 to about 4.5% by weight of the crude product mixture.

Another object of the present invention is to provide an improved process of preparing rabeprazole while the amount of 5-methoxy-2-[[(4-methoxy-3,5-dimethyl-2-pyridinyl)methyl]sulphonyl]-1H-benzimidazole as by-product when the reaction proceeds to completion, is typically within the range of about 1 to about 4.5% by weight of the crude product mixture.

DETAILED DESCRIPTION OF THE INVENTION

Definitions: As used herein, the following abbreviations are used: "VO(acac)$_2$" is vanadium bisacetylacetonate; "TBHP" is tert-butyl hydroperoxide; "NaVO$_3$" is sodium meta-vanadate; "V$_2$O$_5$" is vanadium pentoxide; "MPB" is 5-methoxy-2-[[(4-methoxy-3,5-dimethyl-2-pyridyl)methoyl]thio]benzimidazole; "OMP" is omeprazole; "SOMP" is 5-methoxy-2-[[(4-methoxy-3,5-dimethyl-2-pyridyl)methyl]sulphonyl]-1H-benzimidazole; "Oxone®", refers to a trademark name of an oxidizing agent under Du Pont for an acidic, white, granular, free-flowing solid containing the active ingredient potassium peroxymonosulfate; "TBAB" is tert-butyl ammonium bromide which is a quaternary ammonium salt that is one of the most common phase transfer catalysts; "substantially free" refers to sulphone by-product less than about 1 to about 4.5% by weight of the crude product mixture.

The present invention provides a process for preparing a thioester compound of formula A:

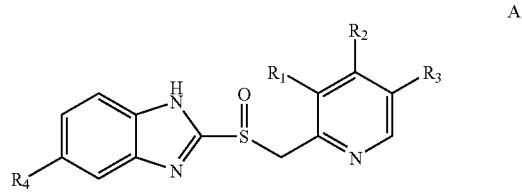

A wherein R$_1$, R$_2$, and R$_4$ are each selected from the group consisting of hydrogen, substituted or unsubstituted lower alkyl and substituted or unsubstituted lower alkoxy; and R$_3$ is selected from the group consisting of hydrogen and substituted or unsubstituted lower alkyl, comprising reacting a thioether compound of formula B

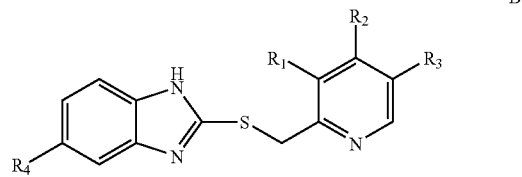

B wherein R$_1$ through R$_4$ are as in formula A, with an oxidizing agent to produce selective oxidation of the thioether compound of formula B to form the thioester compound of formula A.

Preferably, the present invention provides the preparation of substituted 2-(2-pyridylmethyl)sulfinyl-1H-benzimidazoles of formula A, wherein R$_1$ is methyl; R$_2$ is methoxy; R$_3$ is methyl and R$_4$ is methoxy. The compound is omeprazole.

Preferably, the present invention provides the preparation of substituted 2-(2-pyridylmethyl)sulfinyl-1H-benzimidazoles of formula A, wherein R$_1$ is methyl; R$_2$ is 2-trifluoroethoxy; R$_3$ is hydrogen and R$_4$ is hydrogen. The compound is lansoprazole.

Preferably, the present invention provides the preparation of substituted 2-(2-pyridylmethyl)sulfinyl-1H-benzimidazoles of formula A, wherein R$_1$ is methoxy; R$_2$ is methoxy; R$_3$ is hydrogen and R$_4$ is difluoromethoxy. The compound is pantoprazole.

Preferably, the present invention provides the preparation of substituted 2-(2-pyridylmethyl)sulfinyl-1H-benzimidazoles of formula A, wherein $R_1$ is methyl; $R_2$ is $MeOCH_2CH_2CH_2O$, $R_3$ is hydrogen and $R_4$ is hydrogen. The compound is rabeprazole.

According to one embodiment, the oxidation is performed with tert-butyl hydroperoxide (TBHP) in the presence of a catalyst selected from the group consisting of vanadyl bis-acetylacetonate, sodium meta-vanadate and vanadium pentoxide. Preferably, the catalyst is vanadyl bis-acetylacetonate.

According to another embodiment, the molar ratio of tert-butyl hydroperoxide (TBHP) to a compound of formula B, is in the range of about 1.15 to about 4.5. Preferably, the compound of formula A includes 5-methoxy-2-[[(4-methoxy-3,5-dimethyl-2-pyridyl)methyl]thio]-1H-benzimidazole, 2[[[3-methyl-4-(2,2,2-trifluoro-ethoxy)-2-pyridinyl]methyl]thio]-1H-benzimidazole, 5-(difluoromethoxy)-2-[[3,4-dimethoxy-2-pyridinyl)methyl]thio]-1H-benzimidazole, and 2-[[[4-(3-methoxy-propoxy)-3-methyl-2-pyridinyl]methyl]thio]-1H-benzimidazole.

According to another embodiment, the molar ratio of vanadyl bis-acetylacetonate to the compound of formula B is from about 0.01 to about 0.6.

According to another embodiment, the oxidation by tert-butyl hydroperoxide (TBHP) in the presence of a catalyst is performed in an organic solvent selected from the group consisting of toluene, lower alkanols and ethyl acetate.

Another preferred embodiment of the present invention is that the oxidation is performed in an organic solvent such as toluene, a lower alkanol, preferably isopropanol or ethyl acetate. Most preferable solvent is toluene or isopropanol.

Preferably, the oxidation of substituted 2-(2-pyridylmethyl)sulfinyl-1H-benzimidazoles of formula A is performed at temperature ranging from about −10° C. to about 30° C.

Preferably, the oxidation of substituted 2-(2-pyridylmethyl)sulfinyl-1H-benzimidazoles of formula A is performed over a period of about 2 to about 10 hours.

According to another embodiment, the oxidation is performed in the presence of Oxone® (Oxone monopersulphate).

According to another embodiment, the molar ratio between Oxone® (Oxone monopersulphate) and the compound of formula B is from about 1.25 to about 1.6:1, most preferably about 1.4 to about 1.6:1.

According to another embodiment, the oxidation by Oxone® (Oxone monopersulphate) is performed in the presence of an aqueous organic solvent. Preferably, the organic solvent is acetone, methanol or in two-phase system $(CH_2Cl_2/H_2O$, (ethyl acetate/$H_2O$) in the presence of phase-transferred catalyst (e.g. TBAB). More preferably, the oxidation is performed in about 5% aqueous methanol.

Preferably, the oxidation of substituted 2-(2-pyridylmethyl)sulfinyl-1H-benzimidazoles of formula A is performed in a two-phase system selected from ($CH_2Cl_2/H_2O$) and (ethyl acetate/$H_2O$).

Preferably, the oxidation of substituted 2-(2-pyridylmethyl)sulfinyl-1H-benzimidazoles of formula A is performed in the presence of tert-butyl ammonium bromide (TBAB).

According to another embodiment, the oxidation by Oxone® (Oxone monopersulphate) is performed at a temperature ranging from about −10° C. to about 30° C. over a time period of about 2 to about 10 hours.

The oxidation conditions of the present invention result in the production of the compound of formula A, wherein the amount of sulphone derivative is less than about 0.5% (wt/wt) of the final product preferably less than 0.2% (wt/wt).

Preferably, the pure products prepared in according to the disclosed method include pantoprazole, lansoprazole, omeprazole and rabeprazole.

The invention will now be exemplified by the following non-limiting Examples.

EXAMPLES

Example 1

Selective Oxidation of 5-methoxy-2-[[(4-methoxy-3,5-dimethyl-2-pyridyl)methyl]thio]-1H-benzimidazole to form 5-methoxy-2-[[(4-methoxy-3,5-dimethyl-2-pyridyl)methyl]sulfinyl]-1H-benzimidazole (Omeprazole)

1.5 mg (0.6% molar) VO (acac)$_2$ was dissolved in 12 ml ethanol at room temperature. The solution was stirred and 3 grams of 5-methoxy-2-[[(4-methoxy-3,5-dimethyl-2-pyridyl)methyl]thio]benzimidazole (MPB) were added. 1.5 ml aqueous tert-butyl hydroperoxide (TBHP) (70%) was added over a 5-minute period at 16–17° C. and the solution was then stirred for 3 hours. After completion of the reaction, the product mixture was cooled to about 15° C. and treated with aqueous sodium metabisulphate. The resultant solid was filtered off, washed with cooled ethyl acetate to afford the end product as an almost white solid (2.5 grams, yield 79%).

Example 2

Selective Oxidation of 5-methoxy-2-[[(4-methoxy-3,5-dimethyl-2-pyridyl)methyl]thio]-1H-benzimidazole to form 5-methoxy-2-[[(4-methoxy-3,5-dimethyl-2-pyridyl)methyl]sulfinyl]-1H-benzimidazole (Omeprazole)

15 mg (0.6% molar) VO(acac)$_2$ in 5 ml toluene were added to a suspension of 3 grams of 5-methoxy-2-[[(4-methoxy-3,5-dimethyl-2-pyridyl)methyl]thio]benzimidazole (MPB) in 30 ml toluene at a temperature of about 5° C. 3.5 ml of tert-butyl hydroperoxide (TBHP) in toluene (3M, 115%) were added dropwise, while the temperature was maintained between 5 and 7° C. Upon completing the addition of the TBHP, the temperature rose to 22° C. The reaction was allowed to proceed to completion (about 3 hours), after which the cooled product mixture was treated with aqueous sodium metabisulphite. The solid product was filtered off, washed with cooled ethyl acetate and dried in an oven (yield 80.7%)

Example 3

Selective Oxidation of 2-[[[3-methyl-4-(2,2.2-trifluoro-ethoxy)-2-pyridinyl]methyl]thio]-1H-benzimidazole to form 2-[[[3-methyl-4-(2,2,2-trifluoro-ethoxy)-2-pyridinyl]methyl]sulfinyl]-1H-benzimidazole (Lansoprazole)

1.5 mg (0.6% molar) VO (acac)$_2$ is dissolved in 12 ml ethanol at room temperature. The solution is stirred and 3 grams of 2-[[[3-methyl-4-(2,2,2-trifluoro-ethoxy)-2-pyridinyl]methyl]thio]-1H-benzimidazole are added. 1.5 ml aqueous tert-butyl hydroperoxide (TBHP) (70%) is added over a 5-minute period at 16–17° C. and the solution is then stirred for 3 hours. After completion of the reaction, the product mixture is cooled to about 15° C. and treated with aqueous sodium metabisulphate. The resultant solid is filtered off, washed with cooled ethyl acetate to afford the end product as an almost white solid (2.5 grams, yield 79%).

Example 4

Selective Oxidation of 5-(difluoromethoxy)-2-[[(3, 4-dimethoxy-2-pyridinyl)methyl]thio]-1H-benzimidazole to form 5-(difluoromethoxy)-2-[[(3,4-dimethoxy-2-pyridinyl)methyl]sulfinyl]-1H-benzimidazole (Pantoprazole)

1.5 mg (0.6% molar) VO $(acac)_2$ is dissolved in 12 ml ethanol at room temperature. The solution is stirred and 3 grams of 5-(difluoromethoxy)-2-[[(3,4-dimethoxy-2-pyridinyl)methyl]methyl]thio]-1H-benzimidazole are added. 1.5 ml aqueous tert-butyl hydroperoxide (TBHP) (70%) is added over a 5-minute period at 16–17° C. and the solution is then stirred for 3 hours. After completion of the reaction, the product mixture is cooled to about 15° C. and treated with aqueous sodium metabisulphate. The resultant solid is filtered off, washed with cooled ethyl acetate to afford the end product as an almost white solid (2.5 grams, yield 79%).

Example 5

Selective Oxidation of 2-[[[4-(3-methoxy-propoxy)-3-methyl-2-pyidinyl]methyl]thio]-1H-benzimidazole to form 2-[[[4-(3-methoxy-propoxy)-3-methyl-2-pyidinyl]methyl]sulfinyl]-1H-benzimidazole (Rabeprazole)

1.5 mg (0.6% molar) VO $(acac)_2$ is dissolved in 12 ml ethanol at room temperature. The solution is stirred and 3 grams of 2-[[[4-(3-methoxy-propxy)-3-methyl-2-pyridinyl]methyl]thio]-1H-benzimidazole are added. 1.5 ml aqueous tert-butyl hydroperoxide (TBHP) (70%) is added over a 5-minute period at 16–17° C. and the solution is then stirred for 3 hours. After completion of the reaction, the product mixture is cooled to about 15° C. and treated with aqueous sodium metabisulphate. The resultant solid is filtered off, washed with cooled ethyl acetate to afford the end product as an almost white solid (2.5 grams, yield 79%).

Example 6

Changes of Experimental Conditions and Yields

The above described processes of Example 1 and Example 2 were repeated while using the conditions given in Table I below, to give the following results:

Example 7

Comparison with the Method Disclosed by Canadian Patent 1,263.119

4 mg (0.06% molar) VO $(acac)_2$ were added to suspension of 9 grams of 5-methoxy-2-[[(4-methoxy-3,5-dimethyl-2-pyridyl)methyl]thio]-1H-benzimidazole (MPB) in 66 ml ethanol at room temperature. 35 ml of 35% aqueous hydrogen peroxide (150% mol) was added at room temperature with no visible exotherm, the mixture was then stirred. After 12 hours the reaction mixture still contained 65% of untreated MPB and only 32% omeprazole. Prolongation of the reaction time did not lead to further production of omeprazole.

Example 8

Selective Oxidation by Oxone® of 5-methoxy-2-[[(4-methoxy-3,5-dimethyl-2-pyridyl)methyl]thio]-1H-benzimidazole to form 5-methoxy-2-[[(4-methoxy-3,5-dimethyl-2-pyridyl)methyl]sulfinyl]-1H-benzimidazole (Omeprazole)

A mixture of 3 grams 5-methoxy-2-[[(4-methoxy-3,5-dimethyl-2-pyridyl)methyl]thio]benzimidazole (MPB), 3 grams $NaHCO_3$ and 20 ml aqueous methanol was cooled to −2° C. and 3.5 ml (5.69 mmol) Oxone® was added. The mixture was stirred for 4 hours at 0° C. and a further 1 gram (mmol) Oxone® was added and stirring continued for 1.5 hours. A solution of 0.8 gram sodium metabisulfite in 20 ml water was added dropwise over 5–10 minutes. After further stirring the resultant precipitate was filtered, washed successively with water and 50% aqueous methanol and dried.

Yield 2.7 grams, 84% (purity 98.1%), SOMP 0.15%.

Example 9

Changes of Experimental Conditions and Yields

The above described reaction of Example 8 was repeated while using the conditions given in Table II below, to give the following results:

TABLE I

| Catalyst Type/amount (mol %) | TBHP Type/amount | Solvent | HPLC of Product Mixture | | | Yield % |
|---|---|---|---|---|---|---|
| | | | MPB | Omeprazole | Sulfone | |
| $VO(acac)_2$/0.6 | Dry/115% | Toluene | 0.1 | 93.9 | 0.7 | 80.7 |
| $VO(acac)_2$/0.6 | Aq/115% | Toluene | 3.0 | 94.4 | 1.25 | 74.6 |
| $VO(acac)_2$/0.25 | Dry/150% | Toluene | 0.6 | 93.2 | 1.2 | 68.5 |
| $VO(acac)_2$/0.08 | Aq/150% | i-PrOH | 0.9 | 97.2 | 1.6 | 83.5 |
| $VO(acac)_2$/0.05 | Aq/150% | MeOH | 1.9 | 92.1 | 4.4 | >50 |
| $VO(acac)_2$/0.05 | Aq/150% | EtOH | 0.7 | 95.6 | 3.3 | 63 |
| $V_2O_5$silica/0.05 | Aq/450% | EtOH abs | 13.4 | 82.6 | 2.4 | >50 |
| $NaVO_3$/0.6 | Aq/115% | EtOH abs | 7.3 | 87.7 | 1.9 | >50 |

TABLE II

| Oxone® (equivalents to) | Solvent | Temp (° C.) | Time (hours) | % MPB | % OMP | % SOMP | Yield % |
|---|---|---|---|---|---|---|---|
| 1.25 | 5% acetone | −10(2<br>10 | 3<br>0.75 | 0.6 | 97.4 | 0.2 | 60.0 |
| 1.25 | EA/H2O/TBAB | −0(5 | 2 | 0.2 | 94.1 | — | 50.7 |
| 1.25 + 0.35 | 5% MeOH | −2(3 | 7.5 | 0.2 | 98.1 | 0.15 | 84.0 |

Example 10

Selective Oxidation by Oxone® of 2-[[[3-methyl-4-(2,2,2-trifluoro-ethoxy)-2-pyridinyl]methyl]thio]-1H-benzimidazole to form of 2-[[[3-methyl-4-(2,2,2-trifluoro-ethoxy)-2-pyridinyl]methyl]sulfinyl]-1H-benzimidazole (Lansoprazole)

A mixture of 3 grams 2-[[[3-methyl-4-(2,2,2-trifluoro-ethoxy)-2-pyridinyl]methyl]thio]-H-benzimidazole, 3 grams NaHCO$_3$ and 20 ml aqueous methanol is cooled to −2° C. and 3.5 ml (5.69 mmol) Oxone® is added. The mixture is stirred for 4 hours at 0° C. and a further 1 gram (mmol) Oxone® is added and stirring continues for 1.5 hours. A solution of 0.8 gram sodium metabisulfite in 20 ml water is added dropwise over 5–10 minutes. After further stirring the resultant precipitate is filtered, washed successively with water and 50% aqueous methanol and dried. Purity is 98.1%.

Example 11

Selective Oxidation by Oxone® of 5-(difluoromethoxy)-2-[[(3,4-dimethyoxy-2-pyridinjyl)methyl]thiol]-1H-benzimidazole to form 5-(difluoromethoxy)-2-[[(3,4-dimethyoxy-2-pyridinjyl)methyl]sulfinyl]-1H-benzimidazole (Pantoprazole)

A mixture of 3 grams 5-(difluoromethoxy)-2-[[(3,4-dimethyoxy-2-pyridinjyl)methyl]thio]-1H-benzimidazole, 3 grams NaHCO$_3$ and 20 ml aqueous methanol is cooled to −2° C. and 3.5 ml (5.69 mmol) Oxone® is added. The mixture is stirred for 4 hours at 0° C. and a further 1 gram (mmol) Oxone® is added and stirring continues for 1.5 hours. A solution of 0.8 gram sodium metabisulfite in 20 ml water is added dropwise over 5–10 minutes. After further stirring the resultant precipitate is filtered, washed successively with water and 50% aqueous methanol and dried. Purity is 98.1%.

Example 12

Selective Oxidation by Oxone® of 2-[[[4-(3-methoxy-propoxy)-3-methyl-2-pyridinyl]methyl]thiol]-1H-benzimidazole to form 2-[[[4-(3-methoxy-propoxy-3-methyl-2-pyridinyl]sulfinyl]-1H-benzimidazole (Rabeprazole)

A mixture of 3 grams 2-[[[4-(3-methoxy-propoxy)-3-methyl-2-pyridinyl]methyl]thio]-1H-benzimidazole, 3 grams NaHCO$_3$ and 20 ml aqueous methanol is cooled to −2° C. and 3.5 ml (5.69 mmol) Oxone® is added. The mixture is stirred for 4 hours at 0° C. and a further 1 gram (mmol) Oxone® is added and stirring continued for 1.5 hours. A solution of 0.8 gram sodium metabisulfite in 20 ml water is added dropwise over 5–10 minutes. After further stirring the resultant precipitate is filtered, washed successively with water and 50% aqueous methanol and dried. Purity is 98.1%.

A number of embodiments of the invention have been described. The present invention is not to be limited in scope by the specific embodiments described herein. It will be understood that various modifications may be made without departing from the spirit and scope of the invention. Various publications are cited herein, the disclosures of which are incorporated by reference in their entireties.

What is claimed is:

1. A process for preparing a thioester compound of formula A:

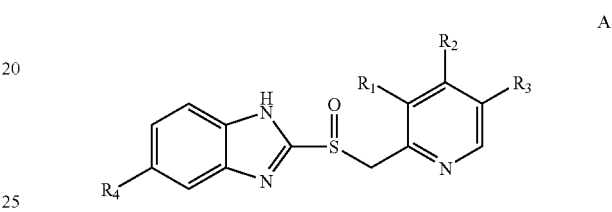

wherein $R_1$, $R_2$, and $R_4$ are each selected from the group consisting of hydrogen, substituted or unsubstituted lower alkyl and substituted or unsubstituted lower alkoxy; and $R_3$ is selected from the group consisting of hydrogen and substituted or unsubstituted lower alkyl, comprising reacting a thioether compound of formula B:

B wherein $R_1$ through $R_4$ are as in formula A, with tert-butyl hydroperoxide in the presence of a catalyst to produce selective oxidation of the thioether compound of formula B to form the thioester compound of formula A, wherein the molar ratio of tert-butyl hydroperoxide to the compound of formula B is in the range of about 1.24:1 to about 4.5:1.

2. The process of claim 1, wherein the catalyst is selected from the group consisting of vanadyl bisacetylacetonate, sodium meta-vanadate and vanadium pentoxide.

3. The process of claim 2, wherein the catalyst is vanadyl bis-acetylacetonate.

4. The process of claim 3, wherein the vanadyl bis acetylacetonate and the compound of formula B is in a molar ratio of about 0.01 to about 0.6.

5. The process according to any one of claims 1, 2, 3 and 4, wherein the oxidation is performed in an organic solvent.

6. The process according to claim 5, wherein the organic solvent is selected from the group consisting of toluene, lower alkanols and ethyl acetate.

7. The process according to claim 5, wherein the oxidation is performed in an organic solvent in the presence of water.

* * * * *